(12) United States Patent
Hallgren et al.

(10) Patent No.: US 8,263,343 B2
(45) Date of Patent: Sep. 11, 2012

(54) PREPARATION OF BIOMOLECULES

(75) Inventors: Elisabeth Hallgren, Uppsala (SE);
Ronnie Palmgren, Stockholm (SE);
Linda Svensson, Upplands Vasby (SE)

(73) Assignee: GE Healthcare Bio-Science AB, Uppsala (SE)

( * ) Notice: Subject to any disclaimer, the term of this patent is extended or adjusted under 35 U.S.C. 154(b) by 1052 days.

(21) Appl. No.: 12/097,311

(22) PCT Filed: Dec. 21, 2006

(86) PCT No.: PCT/SE2006/001479
§ 371 (c)(1),
(2), (4) Date: Jun. 13, 2008

(87) PCT Pub. No.: WO2007/073311
PCT Pub. Date: Jun. 28, 2007

(65) Prior Publication Data
US 2008/0293926 A1    Nov. 27, 2008

(30) Foreign Application Priority Data
Dec. 22, 2005   (SE) ...................................... 0502910

(51) Int. Cl.
*G01N 33/53*   (2006.01)
*C07K 14/00*   (2006.01)
(52) U.S. Cl. ............................................ 435/7.1; 514/2
(58) Field of Classification Search .................. None
See application file for complete search history.

(56) References Cited

U.S. PATENT DOCUMENTS

| 5,093,254 | A | 3/1992 | Giuliano et al. |
| 5,772,888 | A | 6/1998 | Liu et al. |
| 5,907,035 | A | 5/1999 | Guinn |
| 6,454,950 | B1 | 9/2002 | Tjerneld et al. |
| 6,641,735 | B1 | 11/2003 | Yoshizako et al. |
| 2003/0049819 | A1 | 3/2003 | Tjerneld et al. |
| 2003/0205527 | A1 | 11/2003 | Yoshizako et al. |

FOREIGN PATENT DOCUMENTS

| JP | 2000-219698 A | 8/2000 |
| WO | WO 97/05480 | 2/1997 |
| WO | WO 00/58342 | 10/2000 |

OTHER PUBLICATIONS

Hans-Olof et al., "Thermoseparating Water/Polymer System: A novel one-polymer aqueous two-phase system for protein purification", Biotechnology and bioengineering, vol. 66, No. 4, pp. 247-257 (1999).*
Johansson, H.-O., et al., Biotechnology and Bioengineering, 66(4), 247-257, 1999.
Nilsson, et al., Biochimica et Biophysica Acta, 1601, 138-148, 2002.
Persson, J., et al., Bioseparation 9, 105-116, 2000.
Anastase-Ravion, S., et al., Journal of Chromatography B, Sep. 25, 2001, 761(2), 247-254.
Gil, E., et al., Progress in Polymer Science, Dec. 1, 2004, 29(12), 1173-1222.
Lozinsky, V., et al., Trends in Biotechnology, Oct. 1, 2003, 21(10), 445-451.

* cited by examiner

*Primary Examiner* — Anand Desai (57) ABSTRACT

The present invention relates to a method of separating a target from a liquid, which includes providing a polymer in an aqueous liquid, which polymer comprises at least one hydrophobic portion; contacting the polymer-containing liquid with the liquid comprising the target; applying a stimulus to the resulting mixture; and maintaining it until a reversible phase separation is obtained. One phase is polymer-rich and contains target(s) and another phase is polymer-poor. By either maintaining the stimulus, or applying a different stimulus and maintaining it, the polymer-rich phase is transformed into a substantially solid phase.

20 Claims, 4 Drawing Sheets

PREPARATION OF BIOMOLECULES

CROSS-REFERENCE TO RELATED APPLICATIONS

This application is a filing under 35 U.S.C. §371 and claims priority to international patent application number PCT/SE2006/001479 filed Dec. 21, 2006, published on Jun. 28, 2007, as WO 2007/073311, which claims priority to patent application number 0502910-3 filed in Sweden on Dec. 22, 2005.

FIELD OF THE INVENTION

The present invention relates to preparation of biomolecules, such as separation, purification and concentration of proteins. Thus, the invention embraces a method of separating biomolecules, such as proteins; a method of preparing a storage-stable composition comprising biomolecules, such as proteins; a method of purification of biomolecules, such as proteins; and a method of desalting a liquid comprising biomolecules. In addition, the invention also embraces a storage-stable biomolecule composition as such and kits for carrying out the various embodiments of the method according to the invention.

BACKGROUND OF THE INVENTION

Many of the products of biotechnology today are proteins and these proteins must be prepared in large volumes in purified form. The degree of purity required for proteins and other biomolecules for medical use is set by the national regulatory authorities, such as the US Food and Drug Administration (FDA). In addition to purity, the product must retain its biological activity, as the authorities will not certify a production procedure that results in variably active material. Thus, the process must produce the same amount and quality every time. To purify biomolecules, their inherent similarities and differences are often utilised. For example, protein similarity is used to purify them away from the other non-protein contaminants; while differences are used to purify one protein from another. Biomolecules such as proteins vary from each other in size, shape, charge, hydrophobicity, solubility, and biological activity.

One frequently used such method is chromatography, wherein two mutually immiscible phases are brought into contact. More specifically, the biomolecule is introduced into a mobile phase, which is contacted with a stationary phase. The biomolecule will then undergo a series of interactions between the stationary and mobile phases as it is being carried through the system by the mobile phase. The interactions exploit differences in the physical or chemical properties of the components in the sample.

However, sometimes one technique for purifying a biomolecule is not enough. Two or more chromatography steps are often combined in series; and chromatography is advantageously combined with other techniques.

Precipitation is widely used for product recovery of biomolecules especially proteins. The most common type of precipitation of proteins is salt induced precipitation. Protein solubility depends on several factors. It is observed that at low concentration of the salt, solubility of the proteins usually increases slightly. This is termed "salting in". But at high concentrations of salt, the solubility of the proteins drops sharply. This is termed "salting out" and the proteins precipitate out. A second method is the addition of an organic solvent. If there is a medium decrease in the dielectric constant with the addition of an organic solvent, the solubility should decrease also resulting in precipitation. A third method is precipitation by changing the pH of the protein solution. This effect is due to the different functional groups on a protein. There will be some pH, known as the isoelectric point where the net charge on the protein is zero. This is different for different proteins.

A specific example of protein precipitation is found in the purification of immunoglobulins, wherein traditional methods are often based on selective reversible precipitation of the protein fraction comprising the immunoglobulins while leaving other groups of proteins in solution. Typical precipitation agents are ethanol, polyethylene glycol, lyotropic i.e. antichaotropic salts such as ammonium sulphate and potassium phosphate, and caprylic acid. However, these precipitation methods are time-consuming and laborious. Furthermore, the addition of the precipitating agent to the raw material could make it difficult to use the supernatant for other purposes and creates a disposal problem, which is particularly relevant when speaking of large-scale purification of immunoglobulins.

U.S. Pat. No. 5,093,254 (Giuliano et al) relates to aqueous two-phase protein extraction employing polyvinylpyrrolidone (PVP) as the upper phase and maltodextrin as the lower phase. Thus, this is a two-polymer system, which is provided by mixing two aqueous solutions of PVP and maltodextrin at a temperature of 0-8° C. by vigorous mixing followed by centrifugation. The protein to be separated is then added to the two-phase PVP/maltodextrin system to which a dye has been added. The dye may be any amino derivative of triazine dyes, such as Cibacron Blue FGF, Procion Turquoise H-A and Procion Green HE-4BDA. After protein addition, the system is centrifuged to attain phase separation, resulting in the dye strongly partitioned to the upper PVP-containing phase.

The system should be operated at a temperature of 2-6° C. As the dye acts as an affinity ligand to the protein, it is in fact the dye-protein complex which is partitioned to the PVP-containing phase. Consequently, the protein can be extracted by separating the upper phase and elution of protein from dye e.g. by salt addition or pH increase. Thus, the '254 system requires centrifugation, which may affect the structure of more sensitive proteins. In addition, even though the '254 patent argues that their method is a low-cost system, the amount of preparation including mixing the twp polymers and preparing the dye still makes the use relatively time-consuming. In addition, the step of eluting proteins bound to the dye will require additional resources and time. Finally, another disadvantage of this system is the low operating temperature, which will require further demands on the equipment used.

WO 97/05480 (Massachusetts Institute of Technology) relates to a method, device and diagnostic kit for separating and/or concentrating an analyte from a mixture containing one or more contaminants according to size under a two-phase aqueous micellar system. In brief, the method disclosed includes providing at least one surfactant capable of forming a two-phase aqueous micellar system; forming a two phase aqueous micellar system; and permitting the analyte and the contaminant to partition unevenly between the two phases. The surfactant may be non-ionic, such as alkyl poly(ethylene oxide); zwitterionic (dipolar), such as dioctanoyl phosphatidylcholine; or ionic. The principle of excluded-volume interactions is utilised in WO 97/05480, meaning that conditions are selected which drives the majority of the larger reagent of the mixture into the aqueous domain of the micelle-poor phase while smaller reagents are driven into the aqueous domain of the micelle-rich phase. The disclosed method can be used for removing viruses from proteins following fermentation processes, as well as for concentrating viruses for vaccine manufacture or gene therapy.

U.S. Pat. No. 5,907,035 (Baxter Biotech Technology Sarl) relates to methods of purifying proteins having surface active, electron-rich amino acids, particularly histidine, from crude or partially purified protein solutions using an aqueous two phase system. The methods involve the use of polyethylene glycol (PEG), or similar inert hydrophobic molecules, conjugated to a metal chelator such as IDA, which is charged with a divalent metal ligand such as copper. The PEG-chelator-metal complex may be added directly to a crude protein solution containing the target protein. Salts and PEG may then be added and the solution is allowed to form a two-phase system. The target protein is recovered either from the salt or the polymer phase. However, the addition of large quantities of salt is usually a disadvantage, as firstly, salts are well known to denature proteins, and secondly, because a subsequent step for the removal thereof will be required.

WO 00/58342 (Valtion Teknillinen Tutkimuskeskus) relates to isolation and purification of proteins in aqueous two-phase systems (ATPS). Specifically, a process for partitioning proteins is provided by fusing said proteins to targeting proteins which have the ability to carry said protein into one of the phases. A stated advantage of the system is that it is inexpensive as a first or only step, which renders it suitable for the purification of proteins of relatively low market value such as enzymes.

Johansson et al (Hans-Olof Johansson et al: Thermoseparating Water/Polymer System: A Novel One-Polymer Aqueous Two-Phase System for Protein Purification, 1999 John Wiley & Sons) discloses an aqueous two-phase system which uses a linear random copolymer composed of ethylene oxide and propylene oxide groups which has been hydrophobically modified with myristyl groups at both ends (HM-EOPO). This polymer thermoseparates in water, forming an aqueous two-phase system with a top phase composed of almost 100% water and a bottom phase composed of 5-9% HM-EOPO when separated at 17-30° C. The partitioning of three proteins (lysozyme, bovine serum albumin, and apolipoprotein A-1) in the two-phase system was studied, and the amphiphilic protein apolipoprotein A-1 was strongly partitioned to the HM-EOPO phase. The partitioning of hydrophobic proteins can be directed with addition of salt. The possibility of direct protein partitioning between water and copolymer phases shows that this system would be useful for protein separations.

U.S. Pat. No. 6,641,735 (Japan Chemical Innovation Institute) relates to a method for separating a target substance, for example, metal ion, drug or biological component using responsive polymers. According to the method, the surface of a packing undergoes a chemical or physical environmental change under a physical stimulus so that the interaction of a substance interacting with the target substance is reversibly changed in an aqueous solution, thus effecting separation.

However, as the biotechnology fields grows rapidly, and novel biomolecules are frequently presented, there is still a need in this field of alternative and advantageously improved methods for separation, either for combination with the prior art methods in a multi-step protocol of for use separately as single step protocols.

SUMMARY OF THE INVENTION

The present invention solves one or more of the needs discussed above by providing new methods and kits for the preparation of target biomolecules such as proteins.

Thus, one aspect of the present invention is to provide a method of separating one or more target biomolecules from a liquid. This can be achieved by providing a two phase system as described in the appended claims.

An advantageous aspect of the invention is to provide such a method of separating target biomolecules from a liquid, which method that does not require the use of two different polymers.

Another advantageous aspect of the invention is to provide a method of separating target biomolecules from liquid, which method is protein friendly in terms of retaining the biological activity of the target. Thus, the present invention may advantageously be used to separate sensitive proteins.

Another aspect of the present invention is to provide a method of concentrating one or more target biomolecules from a liquid. A specific embodiment of this aspect is a method as discussed above, which results in a storage-stable composition comprising one or more target biomolecules.

A further aspect of the present invention is to provide a method of purifying one or more target biomolecules from a liquid which comprises contaminants and/or impurities. In an advantageous embodiment of this aspect, proteins such as antibodies are purified.

A final aspect of the present invention is a method of desalting a liquid comprising a biomolecule, wherein the method according to the invention is used to reduce the salt contents of a biomolecule preparation.

Further embodiments and advantages of the present invention will appear from the detailed description and claims that follow.

DEFINITIONS

The term "target" means herein any compound, molecule or other entity one wishes to isolate from an aqueous solution. The target may be the desired product or an undesired contaminant in a liquid product.

The term "affinity chromatography" groups means herein groups capable of specific interactions with a target in a principle of 'lock-key recognition'. The target and affinity group will constitute an affinity pair, such as antigen/antibody, enzyme/receptor etc.

Thus, the term "affinity ligands" as used herein will embrace commonly used ligands such as Protein A and Protein G, which are both immunoglobulin-binding proteins.

The terms "antibody" and "immunoglobulin" are used herein interchangeably.

The term "surfactant" is a contraction of "Surface active agent". Surfactants are usually organic compounds that are amphipathic, meaning they contain both hydrophobic groups (their "tails") and hydrophilic groups (their "heads"). Therefore, they are typically sparingly soluble in both organic solvents and water.

The term "polymer" means herein natural and synthetic compounds consisting of repeated linked monomer units. The term "polymer" embraces linear compounds; as well as branched or interconnected compounds, which form a three dimensional network.

The term "hydrophobic" compound or group means herein a compound or group which does not dissolve easily in water, and which is usually non-polar. Oils and other long hydrocarbons are general examples of hydrophobic compounds.

DETAILED DESCRIPTION OF THE INVENTION

The present invention relates to the preparation of biomolecules, such as separation of biomolecules from a liquid and desalting of liquids comprising biomolecules. In this context, it is understood that the term "separation" includes isolation as well as purification.

In a first aspect, the present invention relates to a method of separating at least one target from a liquid, which comprises
(a) providing at least one responsive polymer in an aqueous liquid, wherein the polymer comprises at least one hydrophobic portion;
(b) contacting the aqueous liquid of (a) with the liquid comprising the target(s);
(c) applying at least one first stimulus to the mixture resulting from (b) and maintaining it until a reversible phase separation is obtained, wherein one phase is a polymer-rich phase which comprises at least one target and the other phase is a polymer-poor phase; and
(d) maintaining said stimulus, or, alternatively, applying at least one second stimulus to the polymer-rich phase and maintaining it, until the polymer-rich phase has transformed into a substantially solid phase, and,
(e) isolating the substantially solid phase comprising the target(s).

Thus, the present invention drives for the first time a phase separation of polymers until one phase comprising the polymers and at least one target is substantially solid and hence easily separated from a liquid phase. In this context, the term substantially solid is understood as a phase which can be separated physically from the liquid phase. In a specific embodiment, the polymer-rich phase which comprises at least one target is a solid phase.

In the present specification and claims, it is understood that the terms polymer-rich phase and polymer-poor phase, respectively, refer to phases rich and poor with regard to the responsive polymer. In the context of (a), as the polymer comprises at least one hydrophobic portion, it is understood the liquid provided in (a) need not be a polymer dissolved in the aqueous phase, but the method also includes a dispersion of polymer in the aqueous liquid. The nature and composition of the polymer will be discussed in more detail below. The aqueous liquid is preferably water or an aqueous buffer. It is also understood that in case more than one polymer is provided in (a), such polymers may be partitioned to the polymer-rich phase or the polymer-poor phase, depending on their partition coefficients. In this context, it is understood that the reference to "one polymer" means one kind or type of polymer. The skilled person can easily design a system according to the invention, which results in a substantially solid phase as discussed herein.

The present invention also encompasses an aspect, wherein the method of separating at least one target from a liquid comprises (a) providing at least one responsive polymer in an aqueous liquid, wherein the polymer comprises at least one hydrophobic portion;
(b) contacting the aqueous liquid of (a) with the liquid comprising the target(s);
(c) applying at least one first stimulus to the mixture resulting from (b) and maintaining it until a reversible phase separation is obtained, wherein one phase is a polymer-rich phase comprising target(s) and another phase is a polymer-poor phase;
(d) maintaining the stimulus, or, alternatively, applying at least one second stimulus to the polymer-rich phase and maintaining it, until the polymer-rich phase has transformed into a non-aqueous phase; and,
(e) isolating the non-aqueous phase comprising the target(s).

It is understood that the term "non-aqueous" phase means herein that the major part of the original aqueous liquid content is present in the other phase i.e. in the aqueous phase. However, looking specifically at the polymer-rich phase, in certain embodiments, it may still comprise a relatively large proportion of water or aqueous liquid as compared to the polymer and target. Due to the nature of the responsive polymer, the polymer-rich phase will still constitute a relatively solid or coherent phase, which is advantageously floating on top of the aqueous phase. When operating the present invention, the skilled person may choose how far the phase separation is driven by maintaining the stimuli for a sufficient time period to obtain the desired content of aqueous liquid in the non-aqueous phase. Thus, in one embodiment, the non-aqueous phase may comprise 50-95% of aqueous liquid. In another embodiment, the non-aqueous phase may comprise $\leqq50\%$ aqueous liquid, such as $\leqq40\%$ aqueous liquid, and advantageously $\leqq30\%$ aqueous liquid. In a specific embodiment, the stimulus is maintained until the non-aqueous phase comprises $\leqq10\%$ aqueous liquid. In another specific embodiment, the stimulus is maintained until the non-aqueous phase comprises $\leqq5\%$ aqueous liquid. Thus, in one embodiment, the non-aqueous phase is a solid phase having a very low liquid content relative to the aqueous phase.

In an advantageous embodiment of the present method, the non-aqueous phase comprising polymer and target is substantially dry. In this context, the term "substantially dry" is understood to mean that the non-aqueous phase i.e. the polymer phase is sufficiently dry to be removed from the vessel wherein the two phase separation was carried out without need of filtration or decanting. Thus, the non-aqueous phase may alternatively be denoted a substantially solid phase. As the skilled person will understand, the level of dryness is easily controlled by the stimuli applied such as the duration of heat treatment; the pH applied; or the concentration of salt added, as will be discussed in more detail below.

Below, the details of the present method will be discussed referring to a substantially solid phase as the polymer-rich phase which comprises the target(s). However, it is to be understood that the details below apply equally well to the embodiment wherein the target-containing, polymer-rich phase is discussed as the non-aqueous phase.

In one embodiment of the present method, the polymer-rich phase is the upper phase in (c). In one embodiment, the polymer-poor phase is removed before (d). In an advantageous embodiment, the substantially solid phase is the upper phase in (d). In one embodiment, the stimulus of (d) is maintained until the substantially solid phase comprises $\leqq50\%$ water, based on the total contents of the substantially solid phase. Commonly, this phase will be largely comprised of polymer, target and a certain amount of liquid, which amount will depend upon how far the phase separation is driven by maintenance of the second stimulus. However, even though there may be aqueous liquid present, this phase will still due to the responsive polymer constitute a substantially solid, or fully solid phase. In one embodiment, the substantially solid phase is floating on top of the aqueous phase, and may be lifted off manually, similar to a floating sugar cube.

In one embodiment, (d) comprises applying a stimulus which is different from the stimulus applied in (c). This embodiment is advantageous e.g. in the separation of a target from relatively similar components, such as in the purification of a desired protein from protein contaminants, as the partitioning effect can be efficiently controlled by change of stimuli. In a specific embodiment, two different salts are used to obtain different partitioning coefficients.

In another embodiment, (d) comprises maintaining the first at least one stimulus until the polymer-rich phase has transformed into a substantially solid phase. In this embodiment, no change of condition is required between (c) and (d), as the first phase separation is carried out until the polymer-rich phase has transformed into a substantially solid phase.

Thus, in an advantageous embodiment, (c) and (d) are carried out as a single step wherein the first and the second phase separations are carried out substantially simultaneously or directly following each other, without any change of stimuli. This embodiment is advantageous in terms of effectiveness and ease to perform.

The stimuli applied in the present method may be any physical or chemical stimulus, which causes a chemical and/or physical environmental change sufficient to provide a phase separation as described above. In an advantageous embodiment, the phase separation is reversible.

The stimuli which will cause the polymer to undergo a conformational change resulting in a phase separation may be any stimuli to which the polymer used respond, such as temperature; pH; conductivity (change of ionic strength by changing the concentration and/or kind of salt); solvent composition; light; magnetic field; and electrical field. As the skilled person will understand, the stimulus is selected depending on the nature of the polymer and the system as a whole. In one embodiment, the stimulus of (c) and/or (d) is at least one selected from the group consisting of a temperature change; conductivity change; pH change; and any combination of said stimuli. In one embodiment, at least one stimulus is a change in temperature change provided by increasing the temperature preferably by heating of the liquid comprising polymer and target(s), and the polymer may be defined as a temperature-responsive polymer. Thus, in an advantageous embodiment, the phase separation(s) are obtained without addition of any material to the mixture. This embodiment is especially advantageous if the target is sensitive to additives such as salts. In an alternative embodiment, at least one stimulus is a conductivity change provided by adding at least one salt to the liquid comprising polymer and target(s). In this embodiment, the polymer may be defined as a salt-responsive polymer. In an alternative embodiment, the stimulus is a change of pH, in which case the polymer is denoted a pH-responsive polymer.

In one embodiment, a target is recovered from the substantially solid phase comprising the polymer subsequent to the second phase separation. As the further phase separation is carried out until a practically dry polymer phase is obtained, if desired, the polymer phase may be kept for a period of time before recovery of target. If the substantially solid phase is used as such a storage format, the aqueous phase should be removed before storage. This embodiment will be described in more detail below in the context of the second aspect of the invention. The recovery of target(s) may therefore be provided simply by dissolution of the polymer phase. Thus, in one embodiment, the recovery is achieved by adding a liquid, such as water or a buffer, to the substantially dry polymer phase. The recovery may be carried out directly following the phase separation, after removal of the aqueous phase; or after s suitable period of time.

The target may be any compound, molecule, or other entity such as a biomolecule; an organic compound; or an inorganic compound. The liquid wherein the target is present in (b), i.e. at the contact with the polymer liquid, is advantageously an aqueous liquid such as water or a suitable buffer. If the target is a biomolecule produced in cell culture or fermentation, the target may be present in a cell culture supernatant, a fermentation broth, or a lysate, which is advantageously buffered to suitable conditions. In one embodiment, at least one target is a biomolecule selected from the group consisting of proteins, such as antibodies; peptides, such as oligopeptides or polypeptides; nucleic acids, such as DNA, e.g. plasmid DNA, RNA, or mononucleotides, oligonucleotides or polynucleotides; viruses, such as adenovirus or influenza virus; cells, such as prokaryotic or eukaryotic cells; cell organelles; polysaccharides; liposaccharides; lipids; and carbohydrates. In this context, it is understood that the term "biomolecules" also embraces any fragment of the above exemplified; or any fusion comprising any one of the above mentioned.

Thus, in a specific embodiment, the target is a protein. The protein may be an antibody, such as monoclonal or polyclonal antibodies, e.g. of human or animal origin. Thus, in a specific embodiment, the protein is a monoclonal antibody. The antibody may e.g. be humanized or a chimeric antibody. In a specific embodiment, the target is a monomeric antibody, which is separated from dimers, multimers and/or aggregates of antibodies and/or other components such as ligands which have leaked from a chromatography resin used in a preceding step.

The present method may be used as a single step processing; or as one step in a multi-step process. In one embodiment, the present method is a prefractionation. Prefractionation steps are frequently added to purification schemes where a major contaminant needs to be removed, such as albumin removal in a plasma process for the preparation of antibodies. Thus, in one embodiment, the target is a compound which is removed from a process liquid. This embodiment is also useful as a scavenger step in a purification scheme, such as to remove virus, endotoxin, prions and/or other biomolecules which are often regarded as contaminants. Such a compound may be removed from a method used to purify a target protein, such as a target antibody. In a specific embodiment, the contaminant is an antibody such as IgG removed from blood or blood plasma in order to purify a desired component such as a plasma protein.

The present method may also be used to prepare a format for purification and/or storing ligands, i.e. compounds comprising functional groups capable of interacting with a target. Such ligands may comprise any biomolecule separated according to the present invention, such as protein-containing or peptide-based affinity ligands. Thus, in an alternative embodiment, the target is Protein A or another protein-based affinity ligand. This embodiment will be discussed in further detail below in the context of the third aspect of the invention.

In yet an alternative embodiment, the target is a membrane protein. As is well known, membrane proteins are often difficult to separate using conventional purification methods due to their poor solubility.

The responsive polymer(s) used to affect the phase separation according to the invention are known under many names, such as stimulus-responsive polymers, environmentally sensitive polymers, intelligent polymers or smart polymers. The polymers may be synthetic polymer(s) or natural polymer(s). In an advantageous embodiment, the responsive polymer(s) used in the present method are hydrophobic. In an advantageous embodiment, the polymer(s) present a predominating hydrophobic character, but also comprise one or more hydrophilic portions. Thus, at least part of the polymer used in the present method should be sufficiently hydrophilic to enable the preparation of an aqueous phase comprising responsive polymer(s) as defined under (a). In one embodiment, the polymer(s) will pass through a more to less hydrophobic conformation as said one or more stimuli are applied.

In one embodiment, the responsive polymer(s) used in the present method comprise synthetic polymers and/or copolymers of N-isopropyl acrylamide (NIPAAm). PolyNIPAAm is a thermally sensitive polymer that precipitates out of water at 32° C., which is its lower critical solution temperature (LCST), or cloud point. When polyNIPAAm is copolymerized with more hydrophilic comonomers such as acrylamide, the LCST is raised. The opposite occurs when it is copolymerized with more hydrophobic comonomers, such as N-t-butyl acrylamide. Copolymers of NIPAAm with more hydrophilic monomers, such as AAm, have a higher LCST, and a broader temperature range of precipitation, while copolymers with more hydrophobic monomers, such as N-t-butyl acrylamide, have a lower LCST and usually are more likely to retain the sharp transition characteristic of PNIPAAm. Copolymers can be produced having higher or lower LCSTs and a broader temperature range of precipitation.

In another embodiment, the responsive polymer(s) used in the present method are synthetic polymers based on vinyl monomers, such as acrylic acid (AAc), methacrylic acid (MAAc), maleic anhydride (MAnh), maleic acid (MAc), AMPS (2-Acrylamido-2-Methyl-1-Propanesulfonic Acid), N-vinyl formamide (NVA), N-vinyl acetamide (NVA), aminoethyl methacrylate (AEMA), phosphoryl ethyl acrylate (PEA) or methacrylate (PEMA).

In an alternative embodiment, the present method utilises synthetic polymers such as poly(N-acryloyl-N'-propylpiperazine)(PAcrNPP), poly(N-acryloyl-N'-methylpiperazine) (PAcrNMP), poly(N-acryloyl-N'-ethylpiperazine) (PAcrNEP) or N,N-dimethylaminoethyl methacrylate [DMEEMA].

Other useful synthetic polymers include well known and commercially available polymers such as polyethylene glycol and polypropylene glycol. Another illustrative example is PLURONIC®, a block copolymer based on ethylene oxide and propylene oxide which is available e.g. from BASF.

In a specific embodiment of the present invention, the polymer(s) are natural polymers. Such polymer(s) may be synthesised as polypeptides from amino acids, e.g., polylysine or polyglutamic acid, or derived from naturally occurring polymers such as proteins, e.g., lysozyme, albumin, and casein, or polysaccharides, e.g., alginic acid, hyaluronic acid, carrageenan, chitosan, and carboxymethyl cellulose, or nucleic acids, such as DNA. A further example of a useful natural polymer is elastine. The skilled person can easily prepare such polymers using well known methods. An alternative natural responsive polymer is selected from the group consisting of polymers of agarose, agar, cellulose, dextran, chitosan, konjac, carrageenan, gellan, and alginate. In an advantageous embodiment, the polymer is comprised of a cross-linked polysaccharide, such as cross-linked agarose.

In one embodiment of the present invention, the responsive polymer used in the method consists of an infinite number of monomer units. In another embodiment, the responsive polymer consists of a finite number of monomer units. In another embodiment, the present polymers range in molecular weight from about 1,000 to about 250,000 Da, such as from about 2,000 to about 30,000 Da. Thus, in one embodiment, the molecular weight of the polymer is at least about 1000 Da.

The responsive polymer(s) useful in the present method may be obtained from commercial sources. Alternatively, the skilled person in this field can easily synthesize suitable responsive polymers from monomers using conventional methods.

In brief, well known types of monomers allow the design of copolymer compositions to respond to a specific stimulus and, in some embodiments, to two or more stimuli. In addition, control of molecular weight (by control of reactant concentrations and reaction conditions), composition, structure (e.g., linear homopolymer, linear copolymer, block or graft copolymer, "comb" polymers and "star" polymers) and type and number of reactant end groups permit tailoring of the appropriate polymer.

The polymer(s) used according to the invention may be further modified to improve the responsiveness thereof. Thus, in one embodiment, the responsive polymer(s) have been provided with groups that protonate at certain pKa values, such as amines, such as primary, secondary or tertiary amines, and/or acrylic acid. In a specific embodiment, the responsive polymer(s) comprise responsive groups selected from the group that consists of —COOH groups; —OPO(OH)$_2$ groups; —SO$_3^-$ groups; —SO$_2$NH$_2$ groups; —RNH$_2$ groups; R$_2$NH groups; and R$_3$N groups, wherein R is C.

In a specific embodiment, the present polymers can be derivatized with one or more functional groups, which provide or enforce the character of the polymer such as the hydrophobic character. The most preferred hydrophobic groups in this context are carbon-carbon double bonds, such as found in unsaturated systems, e.g. in alkenes or aromatic systems. The more hydrophobic polymers are advantageously used to separate more difficult targets such as membrane proteins.

In another embodiment, the present polymers can be derivatized pendant light-sensitive groups, the light-sensitive dye, such as aromatic azo compounds or stilbene derivatives. In an advantageous embodiment, light-sensitive polymers and copolymers thereof are synthesized from vinyl monomers that contain light-sensitive pendant groups. Copolymers of these types of monomers are prepared with conventional water-soluble comonomers such as acrylamide, and also with temperature- or pH-sensitive comonomers such as NIPAAm or AAc.

In one embodiment, the polymer comprises functional groups capable of interacting with the target(s), which groups are generally known as ligands. In a specific embodiment, said functional groups are selected from the group consisting of ion exchange groups, such as cation exchangers or anion exchangers; affinity chromatography groups; immobilised metal affinity chromatography (IMAC) groups; reversed phase chromatography (RPC) groups; multimodal ligands which comprise at least two different functionalities capable of interaction with a target; and any combination of said groups.

In an alternative embodiment, one or more of the above described ligands are added to the mixture of (b) to participate in the phase separation free in relation to the responsive polymer. Thus, in this embodiment, the mixture to which stimulus is applied comprises at least one ligand capable of interacting with the target(s).

Ligands comprising one or more functional groups, such as the above-mentioned, may be included in the mixture to undergo phase separation.

In one embodiment, ligands such as affinity groups, IMAC groups or the like are partitioned to the polymer-rich phase, and may be recovered from the substantially solid phase. In one embodiment, the ligands will form complexes with targets, which complexes are then partitioned to the polymer-rich and substantially solid phases. Once the aqueous phase has been removed, the substantially solid phase may be dissolved by adding liquid, such as a buffer which dissociates the complexes and provide the target free in solution. The ligand may be removed by subsequent chromatography. In an alternative embodiment, the dissolved phase is added to a chromatography column which adsorbs the ligand-part of the complexes, and the target is released by adding an eluent.

In another embodiment, ligands are added which due to their partition coefficient in the system are partitioned to the polymer-poor phase. Such ligands may be used to capture undesired compounds, such as contaminants or impurities.

As the skilled person will realise, any marker that facilitates detection and/or subsequent isolation may be included in this embodiment, such as fluorescent markers and the like. Thus, the present method is also useful in diagnostic applications, wherein a sample to be analysed is subjected to the present method and the analyte detected in the dissolved substantially solid phase.

In a second aspect, the present invention relates to a substantially solid phase obtained as described above comprising a responsive polymer and target(s). As mentioned above, the present method is useful to prepare substantially dry and consequently storage-stable preparations of biomolecules. Thus, the present method is advantageously used as an alternative or supplement to freeze-drying. In one embodiment, the substantially solid phase described above is provided in a storage-stable container, such as a plastic package. Storage-stable preparations of target biomolecules may be useful in the drug industry, such as a format wherein a protein drug or vaccine is stored and transported before being administered to a patient. Thus, the invention embraces drug preparations prepared by the herein described method.

In the diagnostic field, a sample may be taken from a patient at one location, which sample is then subjected to the present method to allow transportation in a storage-stable format to a different location, where the analysis is easier performed such as a specialised laboratory. Thus, biomolecule analytes such as antibodies may be detected to allow diagnosis of certain medical conditions.

In a specific embodiment, the method according to the invention is carried out in two or more parallel containers such as the wells of a multiwell plate. Thus, a specific embodiment of the substantially solid phase according to the invention is a multiwell plate or a similar format which contains substantially solid phase in its wells. This embodiment is especially advantageous if multiple analyses of the substantially solid phases are to be carried out. Thus, such a multiwell plate may comprise the same responsive polymer(s) in its wells, but different targets originating from different samples. In an advantageous embodiment, the responsive polymer is cross-linked agarose. Alternatively, the multiwell plate comprises different responsive polymers which have been used to separate the same target.

The present invention embraces a kit comprising, in separate compartments, a polymer comprising a hydrophobic portion; at least one salt; and instruction. The polymer, which is preferably substantially hydrophobic, may be as described above.

In an alternative embodiment, a kit according to the invention comprises, in separate compartments, a substantially solid phase as described above; and instructions for its use in phase separation according to the present invention. Thus, the instructions, which may be in written or recorded form, will describe how to dissolve the polymer phase to recover a target. It is understood that written form includes instructions provided on an electronic media In an advantageous embodiment, one target present in the substantially solid phase comprises Protein A or any other affinity ligand. The target recovered from such a polymer phase may be recovered and used to separated antibodies, antibody fragments or fused antibodies.

In a third aspect, the invention relates to a method of purifying at least one immunoglobulin from a liquid, which method comprises
(a) providing a substantially solid phase according to claim 23, which comprises immunoglobulin-binding ligands, preferably Protein A;
(b) dissolving the substantially solid phase by adding a liquid;
(c) contacting the phase dissolved in (b) with the liquid comprising immunoglobulin and allowing immunoglobulin to bind to the ligands; and,
(d) separating ligand-immunoglobulin complexes from the liquid.

In one embodiment of this method, in (d), the ligand-immunoglobulin complexes are separated by liquid chromatography. In another embodiment, the purified immunoglobulins are recovered in (d) by adding an eluent capable of releasing immunoglobulin from ligands.

In one embodiment, in (d), the ligand-antibody complexes are separated by the method described as the first aspect of the invention. Thus, the details above regarding polymers, stimuli and other conditions can apply to this embodiment.

In an alternative embodiment, in (d), the ligand-antibody complexes are separated by liquid chromatography, wherein the complexes are adsorbed to a separation matrix and the antibodies recovered by elution from the matrix. The principles of liquid chromatography are well known in this field, and the skilled person can easily carry out the separation following standard procedures.

The antibodies purified using the present method may be any one of the above-discussed.

In a fourth aspect, the present invention relates to a method of desalting a liquid comprising at least one target by
(a) providing at least one responsive polymer in an aqueous liquid, wherein the polymer is substantially hydrophobic;
(b) contacting the liquid of (a) with the liquid comprising the target(s)
(c) applying at least one first stimulus to the liquid resulting from (b) and maintaining it until a reversible phase separation is obtained, wherein one phase is a polymer-rich phase comprising target(s) and another phase is a polymer-poor phase;
(d) maintaining said stimulus, and/or applying at least one second stimulus to the polymer-rich phase and maintaining it until the polymer-rich phase has transformed into a substantially solid phase comprising the target(s) and the aqueous phase comprises the majority of the original salt content;
(e) removing the aqueous phase; and, optionally,
(f) dissolving the desalted substantially solid phase in liquid.

The present method of desalting may be carried out using the stimuli, polymers and other conditions discussed above in the context of the first aspect of the invention. Desalting of liquids containing target biomolecules is frequently required in the biotech field, such as of cell culture supernatants and lysates. In one embodiment, the desalting according to the invention is carried out as a step preceding another purification method wherein the salt content should be reduced. As the substantially solid phase is substantially dry and suitable as a storage format; the subsequent purification step need not be carried out directly following the desalting.

Finally, in a last aspect, the invention relates to a method of separating at least one target from a liquid, which comprises
(a) providing at least one polymer gel;
(b) contacting the liquid comprising the target(s) with said gel;
(c) applying at least one first stimulus to the mixture resulting from (b) and maintaining it until a reversible phase separation is obtained, wherein one phase is a polymer-rich phase comprising target(s) and another phase is a polymer-poor phase; and
(d) maintaining said stimulus, and/or applying at least one second stimulus to the polymer-rich phase and maintaining it until the polymer-rich phase has transformed into a non-aqueous phase, and, optionally,
(e) separating the non-aqueous phase comprising the target(s) from the aqueous phase.

In an advantageous embodiment, the gel is provided in a substantially dry form. In a specific embodiment, the gel is comprised of a cross-linked carbohydrate material, such as agarose, agar, cellulose, dextran, chitosan, konjac, carrageenan, gellan, alginate etc. In a specific embodiment, the base matrix is comprised of a cross-linked polysaccharide, such as agarose. Dried agarose is easy to swell by adding liquid such as water. The dried gel may be provided in any suitable vessel, such as one or more parallel containers, preferably the wells of a multiwell plate.

In one embodiment, the gel provided in (a) is the result of a preceding phase separation according to the invention, wherein the polymer was a cross-linked polymer such as cross-linked agarose.

Further details regarding stimulus and other process conditions may be as discussed above. Thus, in one embodiment, the stimulus of (d) is maintained until the non-aqueous phase comprises ≦40% water, such as ≦10% water.

DETAILED DESCRIPTION OF THE DRAWINGS

Figure 1:
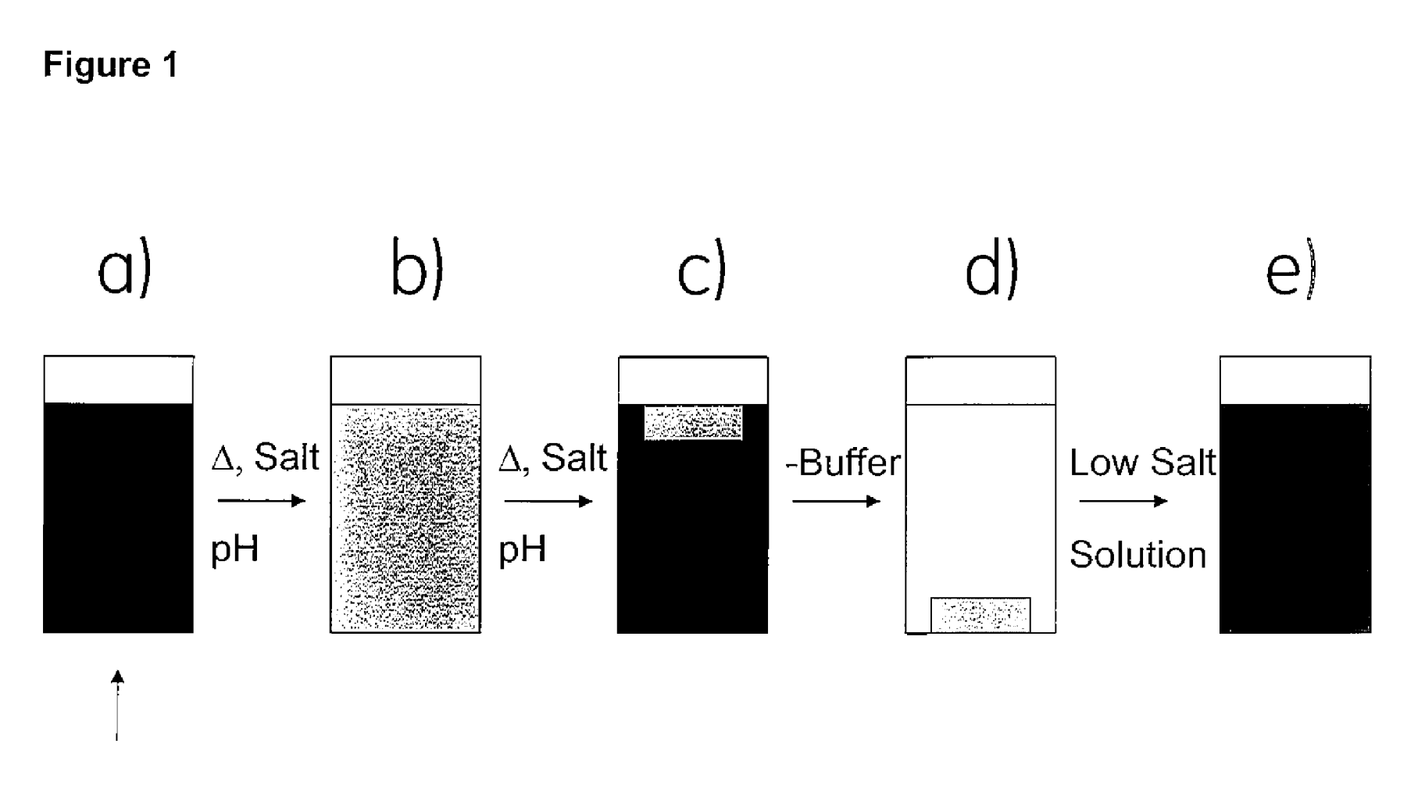
FIG. 1 shows schematically how the method according to the invention can be used. The preparation of the invention is illustrated using a protein as target biomolecule and includes the steps of providing a phase separation by adding stimuli to a liquid phase; adding stimuli to provide a non-aqueous phase comprising the protein and the polymer; and dissolving the non-aqueous phase by adding a buffer.

FIG. 1 shows schematically how the method according to the invention can be used, wherein the preparation of the invention is illustrated using a protein as target biomolecule. More specifically, FIG. 1 shows how a liquid comprising polymer and target protein is provided; how the temperature (A), conductivity (salt) and pH may be changed to provide the first stimuli resulting in phase separation; and how said stimuli are maintained until a non-aqueous phase is formed as an upper phase. The final step of FIG. 1 shows how the non-aqueous phase is dissolved by adding a buffer. If a storage-stable substantially dry biomolecule is desired, the non-aqueous upper phase is withdrawn after step c) and stored. As the aqueous phase is removed after step c), desalting of the final preparation is obtained. Even though FIG. 1 illustrates three stimuli, it is understood that one or more of these may be sufficient for various embodiments of the invention, as discussed elsewhere in the present application.

Figure 2:
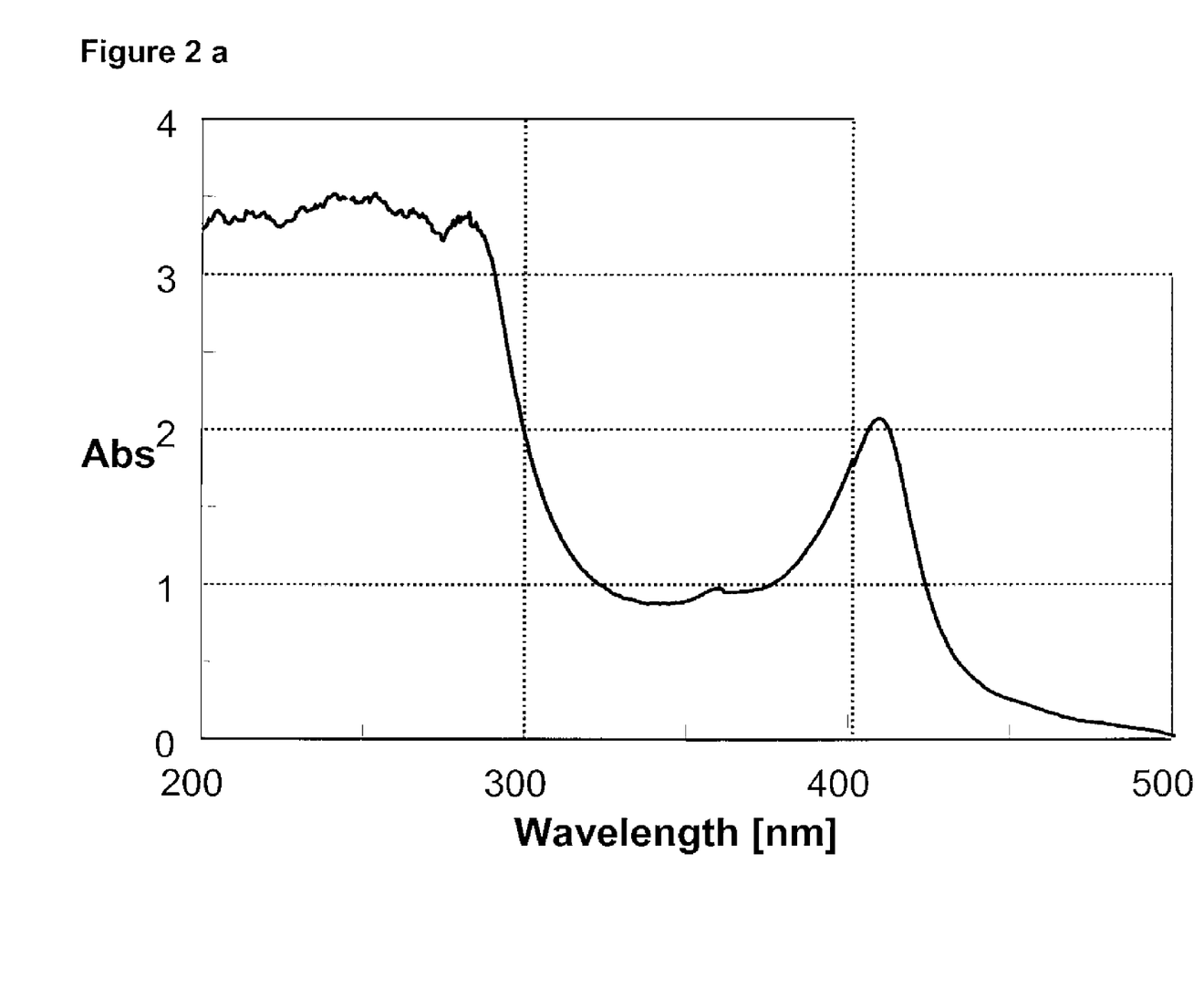
FIG. 2 shows the absorbance curve for myoglobin, obtained as explained in the Example below.

FIG. 2 shows the absorbance curves for myoglobin at 412 nm before a) and after b) the concentration into a non-aqueous phase, obtained as explained in the Example. As appears from FIG. 2, a biomolecule such as myoglobin can be concentrated into a non-aqueous phase by method of the present invention and subsequently dissolved without impairing the protein activity. The absorbance at 412 nm which obtains from the heme group in myoglobin indicates that the protein retains full activity.

Figure 3:
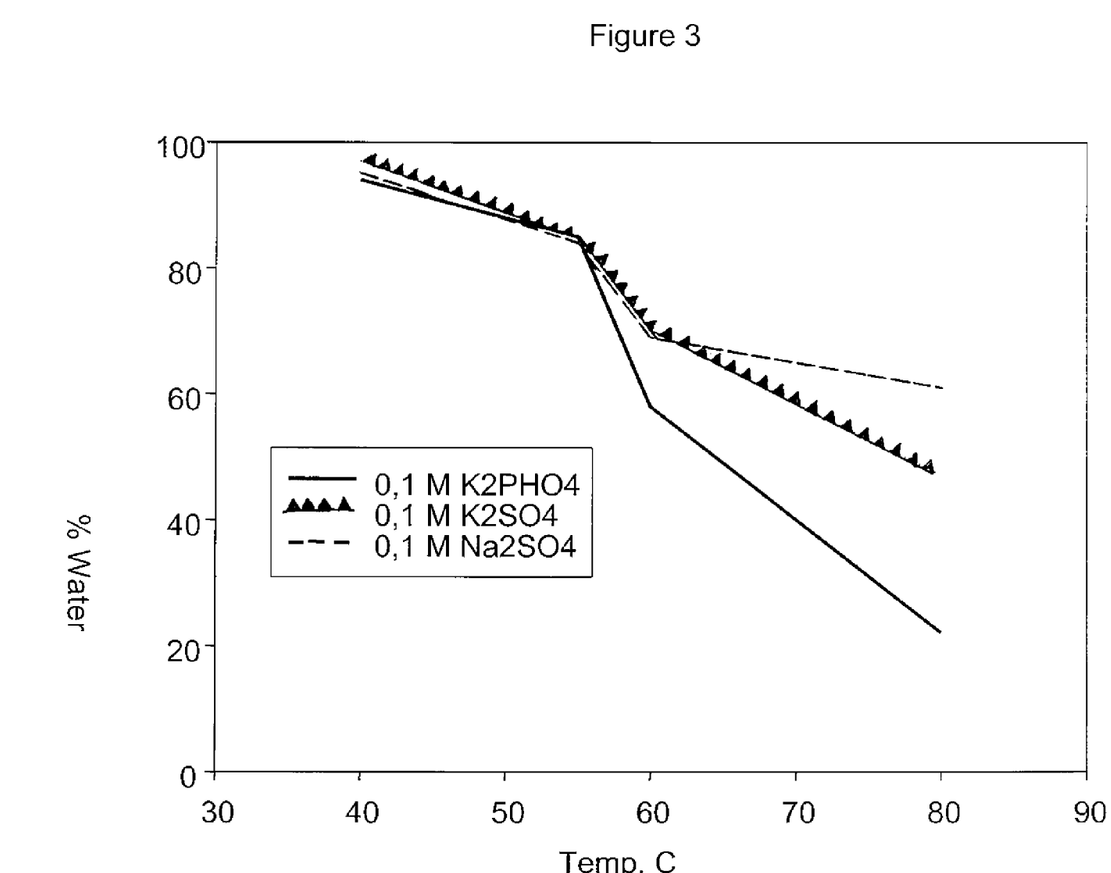
FIG. 3 shows the amount of water in the substantially solid phase and how water can be excluded from the substantially solid phase by a change of stimulus.

FIG. 3 shows the amount of water in the substantially solid phase and how water can be excluded from the substantially solid phase by a change of stimulus (increase of hydrophobicity). In this example, temperature or salt is changed.

EXPERIMENTAL PART

The present examples are provided for illustrative purposes only, and should not be construed as limiting the invention as defined by the appended claims.

Example 1

Synthesis of the Polymer

To prepare the responsive polymer used in this example, 4.96 g isopropylacrylamide (NIPAAm) was dissolved in 10 ml dioxane and put into a round-bottom beaker. 0.298 g t-butylacrylamide, 315 ml acrylic acid and 1.21 g (AMBN) was added to the solution, the solution was purged with nitrogen gas. The reaction was heated up to 70° C. and was allowed to stand for 4 hours. The polymer was purified through precipitation in acetone.

Protein Samples

Myoglobin and Cytochrome C were dissolved in suitable buffers at a concentration of 1 mg/ml. The buffer used were phosphate (pH 7) and acetate (pH 5) and the salts were ammonium sulphate (($NH_4$)$_2SO_4$), potassium sulphate ($KH_2PO_4$) and sodium chloride (NaCl). The salt concentration was varied between 0 and 2 M.

Stability Determination

The protein solution (1 mg/mL) was put in to a cuvette and an absorbance spectrum was recorded on a UV-VIS spectrometer at 412 nm. The absorbance at 412 nm results from the heme group of myoglobin, and indicates that the myoglobin has full activity. In addition, the table also shows that all of the target myoglobin was found in the substantially solid phase.

TABLE 1

| [Myoglobin] mg/ml | ABS Before | ABS Water phase | ABS polymer phase | Mg myoglobin/ 0.2 g polymer | % Myoglobin in the solid polymer phase | ABS Water phase + ABS polymer phase |
|---|---|---|---|---|---|---|
| 0.05 | 0.26 | 0 | 0.26 | 0.035 | 100 | 0.26 + 0 = 0.26 |
| 0.1 | 0.38 | 0.039 | 0.36 | 0.057 | 95 | 0.039 + 0.36 = 0.39 |

This experiment was run at 80° C. in 0.3 M $Na_2SO_4$. The concentration of myogloblin was measured by absorbance at 412 nm.

Separation by Two-Phase System According to the Invention

The polymer was dissolved in the buffer together with the protein at appropriate buffer, salt and pH. The protein solution was put into a cuvette and an absorbance spectrum was recorded on a UV-VIS spectrometer at 412 nm. The temperature was increased until a gel non-aqueous phase in the form of a plug was formed or until the absorbance decreased to zero, which also indicated that a non-aqueous gel plug which contains most of the protein had been formed; the gel plug was floating at the surface. The aqueous phase was removed and the non-aqueous gel plug was dissolved in an aqueous solution to form a new aqueous phase. An absorbance curve for the protein was recorded before and after the experiment to confirm that the protein was stable at these conditions. The results are presented in FIG. 2.

The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims.

The invention claimed is:

1. A method of separating at least one target from a liquid, which comprises:
   (a) providing at least one responsive polymer in an aqueous liquid, wherein the polymer comprises at least one hydrophobic portion;
   (b) contacting the aqueous liquid of (a) with the liquid comprising the target(s) to form a mixture thereof;
   (c) applying at least one first stimulus to the mixture resulting from (b) and maintaining it until a reversible phase separation is obtained, wherein one phase is a polymer-rich phase which comprises at least one target and the other phase is a polymer-poor phase; and
   (d) applying at least one second stimulus, which is different from the first stimulus, to the polymer-rich phase and maintaining it, until the polymer-rich phase has transformed into a substantially solid phase comprising $\leqq 50\%$ aqueous liquid, based on the total contents of polymer, target and liquid of the substantially solid phase, and
   (e) isolating the substantially solid phase comprising the target(s).

2. The method of claim 1, wherein the polymer-rich phase is the upper phase in (c).

3. The method of claim 1, wherein the polymer-poor phase is removed before (d).

4. The method of claim 1, wherein the substantially solid phase is the upper phase in (d).

5. The method of claim 1, wherein the stimulus of (c) and/or (d) is selected from the group consisting of temperature change, conductivity change, pH change, and any combination of said stimuli.

6. The method of claim 5, wherein at least one stimulus is a temperature change provided by heating.

7. The method of claim 5, wherein at least one stimulus is a conductivity change provided by adding at least one salt.

8. The method of claim 1, wherein the majority of target is partitioned to the polymer-rich, substantially solid phase.

9. The method of claim 1, wherein at least one target is recovered from the substantially solid phase.

10. The method of claim 9, wherein the recovery is achieved by dissolving the substantially solid phase in a liquid.

11. The method of claim 10, wherein the substantially solid phase is dissolved in water.

12. The method of claim 1, wherein at least one target is a protein.

13. The method of claim 12, wherein the protein is an antibody.

14. The method of claim 12, wherein the protein comprises at least one immunoglobulin-binding protein, such as Protein A.

15. The method of claim 12, wherein the protein is a membrane protein.

16. The method of claim 1, wherein the responsive polymer is hydrophobic.

17. The method of claim 1, wherein the responsive polymer further comprises one or more hydrophilic portions.

18. The method of claim 1, wherein the mixture to which stimuli are applied comprises at least one ligand capable of interacting with the target(s).

19. The method of claim 1, wherein at least one responsive polymer comprises one or more ligands capable of interacting with the target(s).

20. The method of claim 18, wherein said ligands are selected from the group consisting of ion exchange groups, affinity chromatography groups, immobilised metal affinity chromatography (IMAC) groups, reversed phase chromatography (RPC) groups, multimodal ligands, and any combination thereof.

* * * * *